United States Patent [19]
Astheimer

[11] 3,973,124
[45] Aug. 3, 1976

[54] INFRARED LINE SCANNING INSTRUMENT

[75] Inventor: Robert W. Astheimer, Westport, Conn.

[73] Assignee: Barnes Engineering Company, Stamford, Conn.

[22] Filed: May 19, 1975

[21] Appl. No.: 578,781

[52] U.S. Cl. .............................. 250/334; 250/347
[51] Int. Cl.² .......................................... H01J 31/49
[58] Field of Search ........................... 250/347, 334

[56] References Cited
UNITED STATES PATENTS

| | | | |
|---|---|---|---|
| 3,067,330 | 12/1962 | Hammar | 250/347 |
| 3,519,352 | 7/1970 | Engborg | 250/347 |
| 3,594,578 | 7/1971 | Ohman | 250/347 |
| 3,745,347 | 7/1973 | deBrey et al | 250/347 |

Primary Examiner—Harold A. Dixon
Attorney, Agent, or Firm—Joseph Levinson; Robert Ames Norton

[57] ABSTRACT

An infrared line scanning instrument is provided which scans a single line in a field of view of the instrument. The scan is performed by a scanning mirror which is transparent in the visible and reflective in the infrared region of the spectrum. The infrared radiation is applied to an infrared detector which feeds a display in the form of a light-emitting diode array to light an element in the array in accordance with the amplitude of the IR irradiance seen by the instantaneous field of view throughout the scan. The display is superimposed from the back side of the scanning mirror upon the visible field of view seen by the observer and/or a camera. The instrument thus generates a record of the thermal profile of a single line of a viewed target which is spatially correlated with its location on the target.

9 Claims, 3 Drawing Figures

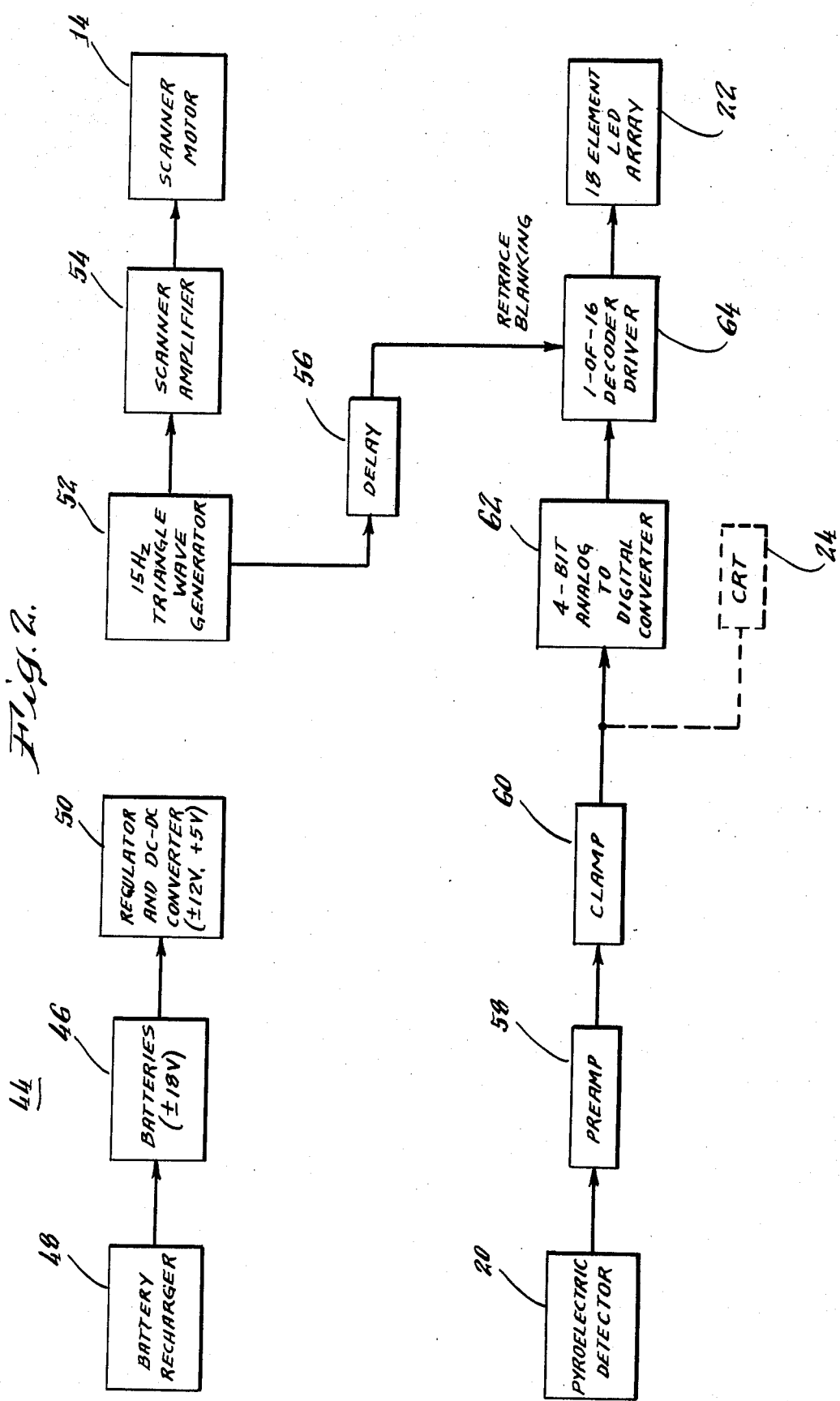

INFRARED LINE SCANNING INSTRUMENT

BACKGROUND OF THE INVENTION

This invention relates to a thermal line scanning instrument, and more particularly to such an instrument which generates a single thermal line scan and displays the thermal profile thereof superimposed on a visual view of the target.

Infrared thermography has been employed extensively for remote temperature sensing and is being utilized in many applications for non-destructive testing of materials and processes, etc., and for diagnostic purposes as well as many other applications. Use of an infrared camera in many of these applications provides a thermal image of the entire target area where, in fact, only a small area or spot of the entire target area may be of interest. It is believed that an infrared camera is used in such applications in order to orient the camera on the subject or target and to identify the objects whose temperature is desired to be examined. For those applications where the IR camera is used primarily to physically locate a small area of interest on the target surface, the expense, bulk, complexity, or other disadvantages in such an application may inhibit the use of the infrared approach.

One approach to the problem is shown and described in U.S. Pat. No. 3,641,348 entitled "Thermal Imaging System with Thermal Image Superimposed on a Target Scene," which is assigned to the assignee of the present application. In this approach, the field of view is scanned by a Nipkow scanner and applied to an infrared detector which modulates a light source in accordance with the intensity of the radiation applied from the field of view which is scanned. The intensity modulated light source is imaged through the same reticle and superimposed on the sight of a viewing telescope. Looking through the telescope a view of the target scene is presented with a red tinge in the regions in which the target is warm or overheated. This system requires a rotating reticle, and also provides for the scanning of the entire target area. Quantitative data with respect to the temperature displayed is not easily interpreted by viewing the target scene in which the temperature is provided in the form of a red tinge. Although the hotter areas would have a brighter tinge than the cooler areas, the differences therebetween would be difficult to interpret.

OBJECTS AND SUMMARY OF THE INVENTION

It is an object of the present invention to provide a novel infrared line scanning instrument which is compact, simpler and less expensive than instruments now available for performing the same or similar functions.

A further object of this invention is to provide a thermal line scanning instrument which is capable of presenting the thermal distribution over a restricted region without requiring a two-dimensional high-resolution infrared camera.

Another object of this invention is to provide a novel thermal line scanning instrument which provides quantitative thermal information on a target scene which may be viewed directly on the target scene by an observer, and readily interpreted.

In carrying out this invention in one illustrative embodiment thereof, a scanning mirror which is transparent in the visible region of the electromagnetic radiation spectrum and reflective in the infrared region scans a line in the field of view of the instrument. The observer views the field of a view of the instrument through the scanning mirror, while an infrared detector is provided for receiving the infrared radiation reflected from the scanning mirror. The output of the infrared detector is quantized and applied to a multielement display means which activates individual elements in the display in accordance with the intensity of the infrared radiation received from the field of view. Radiation from the display means is applied to the back side of the scanning mirror for providing a thermal profile of the scanned line which is superimposed on the field of view of the instrument.

BRIEF DESCRIPTION OF THE DRAWINGS

FIG. 2 shows a block diagram of an illustrative embodiment of the electronics for the thermal line scanner shown in FIG. 1.

DESCRIPTION OF THE PREFERRED EMBODIMENTS

Figure 1:
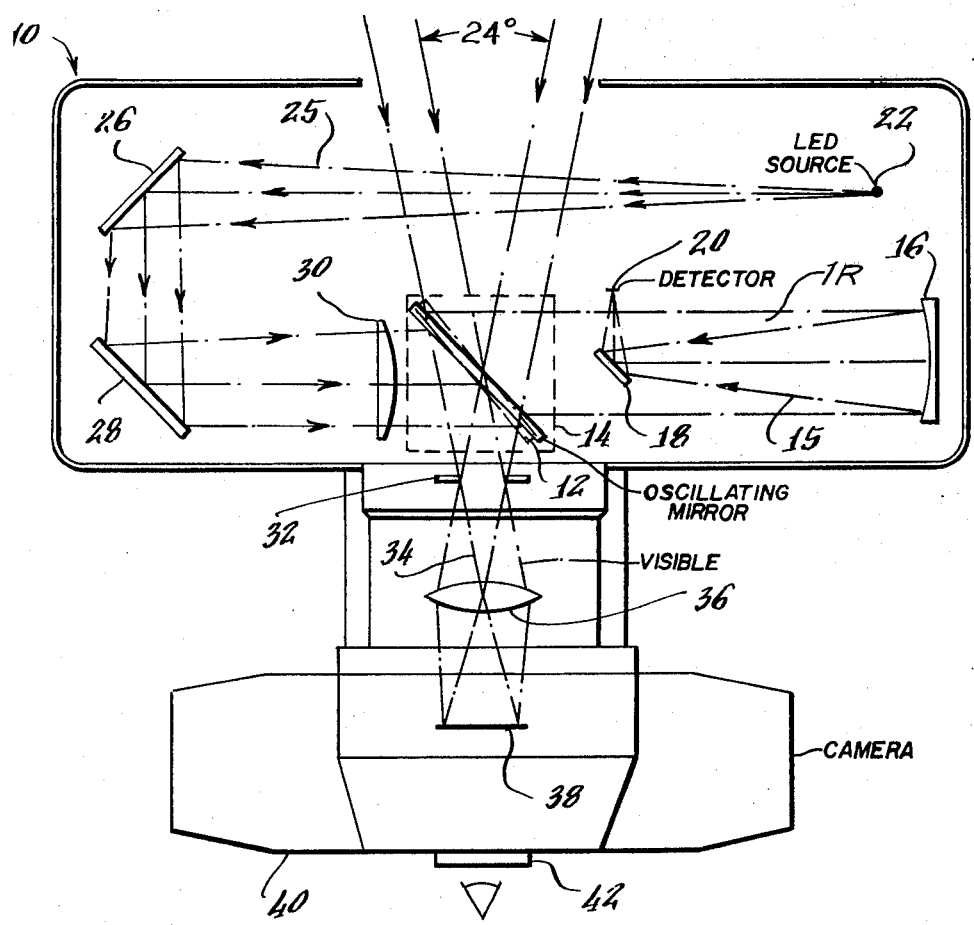
FIG. 1 shows an optical layout of the thermal line scanner in accordance with the present invention.

The thermal line scanner embodied in this invention is shown generally, and indicated by the reference numeral 10 in FIG. 1. The thermal line scanner instrument 10 includes an oscillating scanning flat mirror 12 which is transparent in the blue to yellow visible region of the spectrum and has a reflective gold coating for reflecting red and infrared radiation from 0.65 to 35 micrometers. The scanning mirror 12 is driven by a galvanometer motor 14 which may be, for example, a General Scanning, Inc. G-330 galvanometer motor. Since the scanning mirror 12 is partially transparent in the visible region, the operator may view the target directly or through the reflex sight 42 of a camera 40, through the flat scanning mirror 12.

Figure 3:
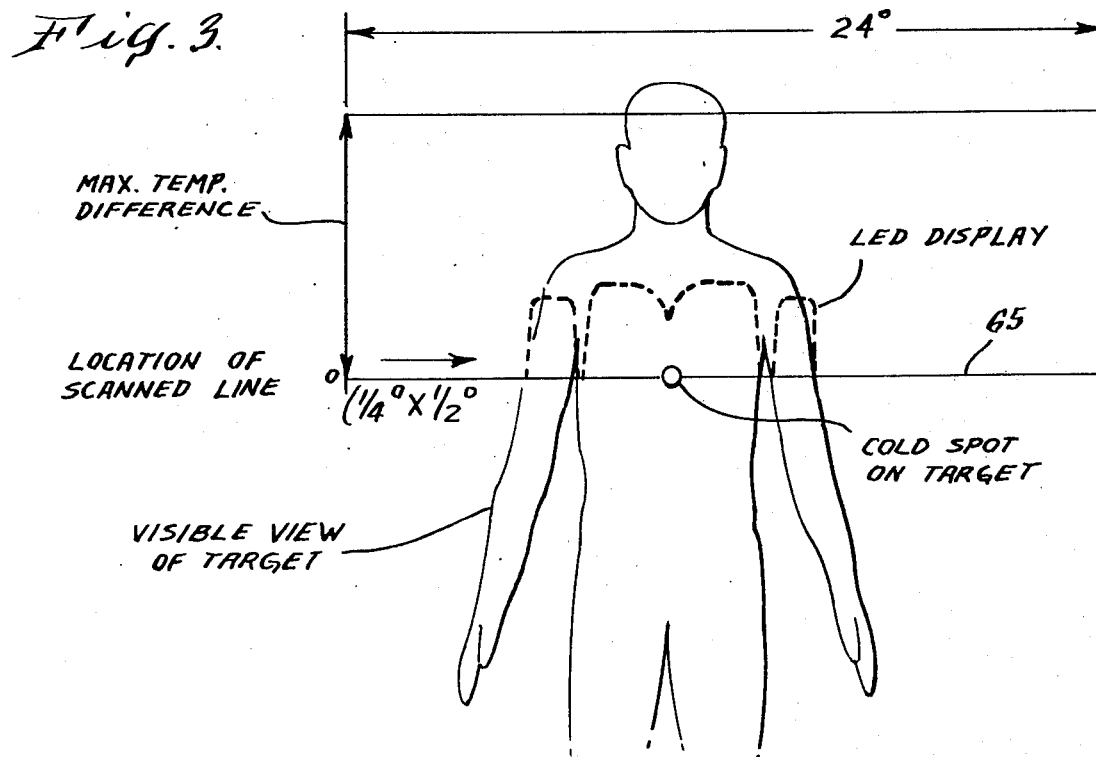
FIG. 3 illustrates the thermal display superimposed on a target view for the thermal line scanner instrument shown in FIG. 1.

Infrared radiation 15 from the field of view is reflected from the scanning mirror to a primary spherical mirror 16, and from there to a secondary flat mirror 18, and applied therefrom to an infrared detector 20. Any suitable infrared detector may be utilized, for example a 0.4 × 0.7 mm DTGS pyroelectric detector is preferable for the current application, although other types of detectors, for example indium antimonide or others, may be utilized. The infrared detector 20 produces an output which varies with the intensity of the radiation applied from the field of view of the instrument. After suitable processing, the signals from the infrared detector 20 are used to drive a multiple element display means which is preferably in the form of a multiple element, light-emitting diode (LED) array 22. The LED array 22 may consist of gallium arsenide phosphide LED's emitting at 0.65 micrometers. As an illustrative example, an 18-element LED array 22 may be utilized and may be type OPE 518 made by Optron, Inc. The diodes in the array 22 are selectively lit in accordance with the amplitude of the signal detected by the infrared detector 20. Radiation 25 from the display 22 is reflected by folding mirrors 26 and 28, and through a collimating lens 30 to the back side of the scanning mirror 12. The array or display 22 is thereby seen through the viewer 42 and appears to the viewer to be scanning across the field superimposed on the target in the field of view of the instrument 10. The lowest (first) and highest (18th) elements in the array or display 22 are always illuminated, thus defining the dynamic range limits of an A-scope type display. The lowest LED also defines the location of the scan line on the target. As the array 22 is scanned across the field, one of the intervening sixteen LED's which is equivalent to the instantaneous analog signal level seen by the infrared detector 20 in that position is illuminated. The viewer accordingly sees an A-scope type display of temperature versus position on one horizontal line in the field of view of the instrument 10 which is clearly identified in the viewer. The thermal or video signal is defined as a 1 part in 18 resolution. The appearance of the display is a dotted wave form which is illustrated in FIG. 3.

As is illustrated in FIG. 1, a camera, for example a Miranda single-lens reflex camera 40, is positioned having a film plane 38 onto which the field of view as well as the superimposed display 22 are imaged so that a permanent recording can be made of the thermal profile on the target scene if so desired. The viewer may still view the field of view through the reflex viewfinder 42 of the camera. A fixed aperture stop 32 is provided for the camera which admits the visible and the LED energy 34 through the lens 36 onto the film plane 38 for recording.

It will be apparent from the above that the LED array or display 22 scans across the field of view in the same direction as the detector 20 from the back side of the scanning mirror 12. This provides perfect synchronization between the IR scan of the field of the instrument 10 by the detector 20 and the LED display 22.

Referring now to FIG. 2, the electronic circuitry for the instrument 10 is considered conventional, and therefore is shown and described in block form. The power supply 44 includes a battery pack 46 which may be charged by a battery charger 48. Battery pack 46 may consist of six 6-volt rechargeable gel electrolyte batteries which in turn drive a regulator and DC to DC converter 50 for producing a 5-volt reference for the digital circuitry which is employed. It will be apparent that other power supplies may be utilized, and in fact an AC supply may be utilized with suitable accompanying circuitry for providing the voltages necessary. A 15-Herz triangular wave generator 52 drives the scanning mirror galvanometer motor 14 through a scanner amplifier 54. The scanning mirror 12 as shown in FIG. 1 may be a General Scanning, Inc. model G-215 with a 1 inch × 1 inch mirror. The scanner motor driving the scanning mirror 12 produces a 15-line per second scan rate. The pyroelectric detector 20 is coupled to a preamplifier 58 which provides a treble boosted frequency response to 1200 Hz, thus making the system response flat from the pyroelectric detector 20 electrical time constant of frequency from 0.05 to 1200 Hz, which maintains the optical resolution along the scan line. The detector signals from the preamp 58 are applied to a clamp circuit 60 which clamps the detector signal to the most negative part, accordingly the lowest temperature on the scan line, to produce a unidirectional display representing temperature deviations from the coldest point in the scan. This circuit also includes an adjustable equivalent temperature offset (ETO) control which allows any part of a large signal to be examined with high gain by adjusting the clamp level. The output of the clamp is provided to an analog-to-digital converter 62 and from there to a decoder driver 64. The analog-to-digital converter 62 and decoder-driver 64 function to quantize the amplitude of the detector signal so that each element or diode in the display or array 22 lights when the signal amplitude falls within the respective limits of that particular element. A delay 56 is coupled between the wave generator 52 and the decoder-driver 64 to provide retrace blanking between scanned lines. In the 18-element LED array 22, the lowest, or first, LED is aligned optically conjugate with the detector 20 and always activated, thus indicating the horizontal line in the field whose temperature profile is being displayed. This will be seen in FIG. 3, and is identified by line 65 which corresponds to the lighting of the first LED in the array 22, with the detector signal 20 being clamped on the coldest spot on a target being viewed. The visible view of the subject is seen through the viewer 42 of the camera. As will be seen in FIG. 3, the LED display is superimposed on the target scene, giving a clear thermal profile of the scanned line.

It will be apparent that the display may include more or fewer diodes, as required. The number of diodes utilized will determine the number of temperature intervals in a linear range which are quantized, but are not necessarily required to be equal. In any event, the first and last diodes would always be lit to indicate the range limits of the instrument. The LED diodes are operated as on-off devices with the temperature being indicated by the specific LED being activated in the array. Alternative displays are possible. A small cathode ray tube 24 as shown in dotted form on FIG. 2 could be used in place of the diodes, which would give a continuous rather than an amplitude-quantized trace. However, this requires a high voltage supply, and eliminates the quantization which may be more desirable than a continuous trace for certain applications. Instead of recording the scene on a film, as illustrated, the camera could be replaced by a vidicon and the display presented on a television monitor.

An alternative mode of operating the LED display would be to cause all of the diodes to light in a chain up to the one indicating the amplitude of the signal on the detector. This mode would tend to illuminate the entire area between the base line and the temperature profile, but may produce some scene obscuration, which may be objectionable.

The instrument described has a size of 9.25 inches × 3.75 inches × 6 inches and weighs 11.75 lb. including the batteries and a camera. By eliminating the batteries, 3.3 lbs. would be subtracted from the overall weight. The instrument 10 operates at a frame rate of 15 per second, with a scan field of 25° × 0.43°, and an angular resolution of 0.25° × 0.43° high. The compactness and the light weight characteristics of the instrument make it quite suitable for hand-held operation, and provide a portability feature which is difficult to achieve in other types of scanning radiometers or IR cameras. It will be apparent that the instrument may be mounted on a tripod or other suitable support if desired.

Since other modifications and changes, varied to fit particular operating requirements and environments, will be apparent to those skilled in the art, the invention is not considered limited to the examples chosen for purposes of illustration, and covers all changes and modifications which do not constitute departures from the true spirit and scope of this invention.

I claim:

1. An infrared line scanning instrument for scanning a line on a target in the field of view of the instrument and superimposing the thermal profile of the scanned line on a visual view of the target comprising, in combination, a. a scanning mirror and scanning means for scanning said scanning mirror over a line of the field of view of said instrument, b. said scanning mirror being transparent in the visible region of the electromagnetic radiation spectrum and reflective in the infrared radiation region, c. viewing means for observing the field of view of said instrument through said scanning mirror, d. infrared detector means for receiving infrared radiation from the field of view of said instrument reflected from said scanning mirror, e. a multiple element display means, f. means coupling said infrared detector means to said multiple element display means for activating elements in said display means in accordance with the intensity of the infrared radiation applied to said infrared detector means from the field of view of said instrument, and g. means for applying radiation from activated elements in said display means to the back side of said scanning mirror whereby the thermal profile of the scanned line is superimposed on the field of view of said instrument in said viewing means.

2. The structure set forth in claim 1 wherein said scanning mirror is provided with a reflective coating which is transparent in the blue to yellow visible region of the spectrum and reflective in the red and infrared regions of the spectrum.

3. The structure set forth in claim 1 wherein said display means comprises a plurality of light emitting diodes.

4. The structure set forth in claim 1 wherein said display means comprises a cathode ray tube.

5. The structure set forth in claim 1 wherein said viewing means comprises a camera with a reflex sight for viewing and recording said thermal profile of the scanned line superimposed on the field of view.

6. The structure set forth in claim 1 wherein said viewing means comprises a vidicon.

7. The structure set forth in claim 1 wherein said infrared detector means comprises a pyroelectric detector.

8. The structure set forth in claim 3 wherein said plurality of light emitting diodes are arranged in a linear array, said first diode in said array being continuously illuminated to indicate the position of said scanned line.

9. The structure set forth in claim 8 wherein the last diode in said array is continuously illuminated to indicate the range limits of the instrument between said first and said last diode in said linear array.

* * * * *